United States Patent [19]
Seliger et al.

[11] Patent Number: 5,902,878
[45] Date of Patent: May 11, 1999

[54] MODIFIED PHOSPHORAMIDITE PROCESS FOR THE PRODUCTION OF MODIFIED NUCLEIC ACIDS

[75] Inventors: Heinz-Hartmut Seliger, Elchingen-Thalfingen; Sibylle Berner, Augsburg; Klaus Mühlegger, Polling; Herbert Von Der Eltz, Weilheim; Hans-Georg Batz, Tutzing, all of Germany

[73] Assignee: Boehringer Mannheim GmbH, Mannheim, Germany

[21] Appl. No.: 08/934,018

[22] Filed: Sep. 19, 1997

Related U.S. Application Data

[62] Division of application No. 08/370,836, Jan. 10, 1995, Pat. No. 5,700,919, which is a continuation of application No. 08/933,589, Aug. 26, 1992, abandoned, which is a continuation of application No. 07/528,204, May 24, 1990, abandoned.

[30] Foreign Application Priority Data

May 24, 1989 [DE] Germany .............................. 39 16 871

[51] Int. Cl.$^6$ .............................. C07H 1/00; C07H 21/00
[52] U.S. Cl. ....................... 536/22.1; 536/23.1; 536/24.3; 536/24.33; 536/25.3; 536/25.31; 536/25.32; 536/25.33; 536/25.34; 435/6; 435/91.1
[58] Field of Search ................................... 536/22.1, 23.1, 536/24.3, 24.33, 25.3, 25.31, 25.32, 25.33, 25.34; 435/91.1, 6

[56] References Cited

U.S. PATENT DOCUMENTS

| | | | |
|---|---|---|---|
| 4,415,732 | 11/1983 | Caruthers et al. | 536/27 |
| 4,547,569 | 10/1985 | Letsinger et al. | 536/29 |
| 4,816,569 | 3/1989 | Miyoshi | 536/29 |
| 5,700,919 | 12/1997 | Seliger et al. | 536/22.1 |

FOREIGN PATENT DOCUMENTS

| | | |
|---|---|---|
| 0 097 373 A2 | 1/1984 | European Pat. Off. . |
| 0 117 777 B1 | 9/1984 | European Pat. Off. . |
| 0 136 543 B1 | 4/1985 | European Pat. Off. . |
| 0 152 459 B1 | 8/1985 | European Pat. Off. . |
| 0 169 787 A1 | 1/1986 | European Pat. Off. . |
| 0 173 251 A2 | 3/1986 | European Pat. Off. . |
| 0 216 357 A3 | 4/1987 | European Pat. Off. . |
| 0 251 283 A2 | 1/1988 | European Pat. Off. . |
| 0 278 220 A1 | 8/1988 | European Pat. Off. . |
| 0 285 058 A2 | 10/1988 | European Pat. Off. . |
| 0 304 215 | 2/1989 | European Pat. Off. . |
| 36 42 939 A1 | 12/1987 | Germany . |
| A 59-141598 | 8/1984 | Japan . |
| A 61-57596 | 3/1986 | Japan . |
| T 3-500248 | 1/1991 | Japan . |
| WO 84/03285 | 8/1984 | WIPO . |
| WO 86/07363 | 12/1986 | WIPO . |
| WO 88/ 0431 | 6/1988 | WIPO . |

OTHER PUBLICATIONS

Thuong et al., Biochime, 67, pp. 673–684, 1985, "Chemical synthesis of natural and modified oligodeoxynucleotides".

Barker et al., J. Biol. Chem., 246, pp. 7135–7147, "Agarose Derivatives of Uridine Diphosphate and N–Acetylglucosamine for the Purification of Galactosyltransferase".

Cuatrecasas, J. Biol. Chem., 245, pp. 3059–3065, 1970, "Protein Purification by Affinity Chromatography".

Jäger et al., Biochemistry, 27, pp. 7237–7246, 1988, "Oligonucleotide N–Alkylphosphoramidates: Synthesis and Binding to Polynucleotides".

Bannwarth et al., Tetrahedron Letters vol. 30, No. 12, pp. 1513–1516, 1989, "A simple specific labelling for oligonucleotides by bathophenanthroline–Ru" Complexes as nonradioactive label molecules.

Asseline et al., Nucleosides & Nucleotides, 7, pp. 431–455, 1988, "Oligothymidylates Substitues Par Un Derive De L'Acridine en Position 5', A la fois en Position 5' et 3' ou sur un Phosphate" Internucleotidique.

Gait, Oligonucleotide Synthesis, IRL Press, Oxford, 1994, pp. 35–49, "Solid–phase Synthesis of Oligodexyribonucleotides by the Phosphite–triester Method".

Hamamoto et al., Chemistry Letters, pp. 1401–1404, 1986, "New Approach to the Synthesis of Deoxyribonucleoside Phosphoramidite Derivatives".

Zuckerman, Nucleic Acids Research, vol. 15, No. 13, pp. 5305–5321, 1987, "Efficient methods for attachment of thiol specific probes to the 3'-ends of synthetic oligodeoxyribonucleotides".

*Primary Examiner*—James O. Wilson
*Attorney, Agent, or Firm*—Nikaido Marmelstein Murray & Oram, LLP

[57] ABSTRACT

The subject matter of the invention is a modified phosphoramidite process for the synthesis of nucleotide sequences. By use of a modified nucleoside phosphoramidite it is possible to produce nucleotide sequences which have a modified phosphate residue.

12 Claims, No Drawings

5,902,878

MODIFIED PHOSPHORAMIDITE PROCESS FOR THE PRODUCTION OF MODIFIED NUCLEIC ACIDS

This is a division of application Ser. No. 08/370,836, filed Jan. 10, 1995, now U.S. Pat. No. 5,700,919 which is a continuation of Ser. No. 08/933,589, filed Aug. 26, 1992, now abandoned, which is a continuation of Ser. No. 07/528,204, filed May 24, 1990, now abandoned.

BACKGROUND OF THE INVENTION

The subject matter of the present invention relates to a modified phoshoramidite process for the production of modified nucleic acids and new compounds which are used in this process.

DESCRIPTION OF THE PRIOR ART

Nucleic acids are a group of compounds which are of fundamental importance for life in the world and are therefore present in all organisms. The genetic information is stored in them. They are also a criterium for the differentiation and identification of different species of organisms, since the nucleic acid sequences are characteristic for each organism. There has therefore been no lack of attempts to synthesize as well as to detect nucleic acids.

Nucleic acids can be synthesized chemically or enzymatically. The chemical synthesis of the naturally occurring nucleic acids in the β configuration has recently gained even more in significance since such large amounts of nucleic acids with a defined nucleotide sequence can be produced. The chemical synthesis has been able to establish itself in particular for the synthesis of oligonucleotides in the β configuration. The different methods can be distinguished according to the type of the nucleotide building blocks used and the reaction steps for attachment to the neighbouring nucleotide in the sequence:

In the phosphodiester method a nucleoside monophosphate, in which all reactive groups with the exception of the phosphate residues are protected, together with a coupling agent, for example a trialkylarylsulphonic acid chloride, is reacted with a further nucleoside in which all reactive groups, except for the hydroxy group at which the reaction is to take place, are protected. The yields in this method are low, primarily because during the condensation steps to build the oligonucleotide chain undesired side reactions occur at the non-esterified OH-groups of the internucleotide (phosphate) linkages and result in complex reaction mixtures. Furthermore, it has the major disadvantage that the phosphoric acid diesters formed are only soluble in a few protic solvents in which the esterification has to be carried out. Such solvents like pyridine, dimethylformamide or dimethylsulphoxide have well-known disadvantages such as e.g. high boiling points. As a result of the polar character of the phosphodiester derivatives the isolation and purification has to be carried out over ion-exchangers and cannot be carried out in a simple way e.g. over silica gel using solvents with low boiling points (such as e.g. dichloromethane).

The disadvantage of the insolubility of the products in a multitude of organic solvents is avoided by the phosphotriester method.

The phosphotriester method uses one phosphoric acid derivative which has only 1 reactive group, but 2 hydroxy groups next to the phosphorus atom which are protected with different protecting groups. After the reaction with the first nucleoside one of the protecting groups is cleaved off and the hydroxy group formed can then be activated for the reaction with the second nucleoside. As a consequence of this procedure it is necessary to carry out two additional reaction steps on the nucleoside phosphate which leads to a reduction in the yield of activated nucleoside phosphate.

A particularly advantageous method which manages with fewer reaction steps on the relatively expensive synthetic building blocks has become known as the phosphoramidite process (Gait, M. J. et al., Oligonucleotide Synthesis: A Practical Approach, IRL Press Oxford). In this procedure no phosphoric acid derivatives but rather derivatives of phosphorous acid, the so-called phosphoramidites, are used. The following residues are attached to the trivalent phosphorus atom:

a reactive group, for example a halogen atom, which enables the linkage with the first nucleoside, a secondary amino group with which the linkage with the second nucleoside can be effected after activation and a hydroxy group masked by a protecting group.

In the first step of the phosphoramidite process the phosphorous acid derivative is reacted with a first nucleoside; in this process the nucleoside replaces the reactive group. In the second step the secondary amino group is replaced selectively by the second nucleoside. A tetrazole is usually used as the activating reagent in the second step. In a subsequent step the nucleotide sequence is oxidized, for example with iodine, and the protecting group is cleaved off. In one variant, the phosphoramidite process has been described as a solid phase process. In this variant the growing nucleotide sequence is bound to a solid phase. The separation of excess synthetic reagents and building blocks as well as the purification of the oligonucleotide sequence is greatly simplified by this means. Commercially available automated nucleic acid synthesizers work according to this procedure. Their construction has e.g. been matched to specific steps of the phosphoramidite process.

Nucleic acids with a known nucleotide sequence have in particular been applied for the specific detection of DNA in biological sample material.

In such methods of detection use is made of the property that the single strands of nucleic acids can react with other single-stranded nucleic acids to form a double strand if the single strands have nucleotide sequences which are complementary to each other and both have the same configuration at the C-1 of the ribose ($\alpha$ or $\beta$). Since the nucleic acids which occur naturally have the β configuration with regard to the linkage of bases and sugars, the β nucleic acids in particular may be considered as complementary nucleic acids. This process of double strand formation is called hybridization.

The formation of a double strand can be detected if a modified single-stranded complementary nucleic acid is used for the hybridization with the single-stranded nucleic acid. Afterwards the amount of the hybridized nucleic acids is determined via the modification which can for example be a radioactive label.

For the synthesis of modified nucleic acids either a natural nucleic acid which is already available can be chemically or enzymatically modified or the nucleotide sequence can be synthesized with the aid of nucleotide building blocks which have already been modified.

However, by modifying the ends of already completely synthesized nucleic acids, as suggested for example for the 5'-end in WO 86/07363, nucleic acids can be prepared which only contain a single modified nucleotide per single strand.

Methods for determining the amount of nucleic acids with this type of modified nucleic acids as probes are therefore less sensitive.

Therefore it was suggested in the EP-A 0173251 that the bases of complete nucleic acids be modified by chemical reactions. However, several reaction steps on the nucleic acid are necessary for this and the rate of modification is dependent on whether the nucleic acid contains bases with free amino groups, the modification of which does not impair the ability to hybridize with complementary nucleic acids.

The preparation of a dinucleotide which has a modification at the phosphorus atom is described in Jäger et al. (Biochemistry Vol. 27, p. 7237 (1988)). The modification consists of a primary amino group bound via a linker and is introduced into a process similar to the usual phosphoramidite process.

However, this process cannot be carried out on the usual automated synthesizers which use the phosphoramidite method. A further disadvantage is that no more additional nucleotides can be joined on because the free amino group reacts with the electrophilic reagents which are used for this.

Each of the available state-of-the-art methods therefore has considerable disadvantages.

SUMMARY OF THE INVENTION

The object of the present invention was to avoid the disadvantages of the known processes and in particular to make available a process for the synthesis on solid phases of nucleic acids in the β configuration which are modified at the phosphate residue which can be carried out with simple starting materials in few reaction steps with high yields.

An object of the invention is a process for the preparation of a nucleotide sequence according to formula IX

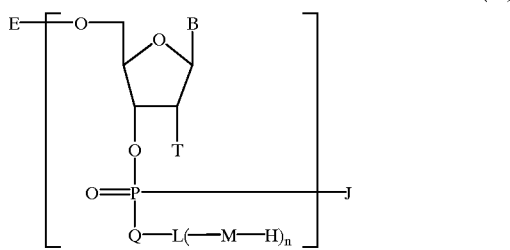

(IX)

wherein

E is selected from the group consisting of hydrogen and a phosphorous atom in the phosphate residue of an adjacent nucleotide or oligonucleotide;

J is selected from the group consisting of hydroxy, a 5' oxygen atom of the sugar of an adjacent nucleotide or oligonucleotide and an oxygen chemically bound to a carrier;

B is a natural or modified nucleobase;

T is selected from the group consisting of hydrogen, hydroxy, lower alkyl, lower alkyloxy and azide;

Q is oxygen or sulfur;

L is a (n+1) valent bridging link;

M is selected from the group consisting of oxygen, sulfur, nitrogen and NH; and n is a natural number from 1 to 200;

comprising reacting a compound according to formula I

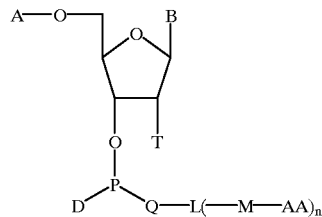

(I)

wherein

A is selected from the group consisting of an oxygen protecting group, a nucleotide and an oligonucleotide;

B, Q, L, T, M, and n are as described above;

D is a secondary amine residue; and

AA is a cleavable protecting group;

with a nucleoside which has a free 5' hydroxyl group and oxidation of the polynucleotide so formed.

The lower alkyl and lower alkoxy groups contain 1 to 6, preferably 1 to 4 carbon atoms.

As evident from the components of this reaction, in formulas V and IX at least one of E and J means a further nucleotide or nucleotide sequence.

Processes for the production of nucleic acids by the so-called phosphoramidite process are known in principle, for example from Biochimie 1985, 67, 673–684. The process of the present invention differs in particular from the state-of-the-art processes in that a novel nucleoside phosphoramidite, namely that of formula I, is used as the starting material.

DETAILED DESCRIPTION OF THE INVENTION

A preferred residue E in formula I is an oxygen protecting group. Protecting groups which are suitable for the protection of the 5'-hydroxy group in nucleotide syntheses are known. Protecting groups such as the triphenylmethyl group or the dimethoxytriphenylmethyl group which can be cleaved off under acidic conditions are used particularly often.

If the residue E represents a nucleotide or oligonucleotide it can either be a natural or a modified nucleotide or oligonucleotide. The nucleotides are preferred to the oligonucleotides because the synthesis using oligonucleotides is more laborious. The nucleotides or oligonucleotides of the residue E can also be residues prepared according to the invention. Reactive groups of the nucleotides or oligonucleotides of the residue E are preferably protected by suitable protecting groups. In particular the terminal 5'-hydroxy group of the nucleotide or oligonucleotide of the residue E is protected by an oxygen protecting group. This oxygen protecting group has in particular the meaning mentioned above for residue E.

The natural nucleobase of the residue B is preferably adenine, thymine, cytosine, uracil or guanine. The modified bases can for example be bases altered in their structure in the ring or in the substituents. Examples are 7-deazaguanine or 5-aminoalkyluracil or 8-aminohexyl-amino-adenine. Those bases are preferred in which the Watson-Crick base-pairing with a complementary nucleic acid is not influenced or only to a very slight extent.

The residue T can have the ribo or arabino configuration. The ribo configuration is preferred. Groups which can be cleaved off under basic, acidic or nucleophilic conditions, preferably the t-butyldimethylsilyl or triisopropylsilyl group, are suitable as the protecting group for the hydroxy residue.

The protecting group AA is preferably a protecting group which can be selectively cleaved off. A protecting group is preferred which can be cleaved off simultaneously under the conditions under which the complete nucleotide sequence is cleaved from the solid carrier. Therefore protecting groups which can be cleaved off under acidic conditions, as denoted for instance in E, are not preferred. Particularly preferred are therefore protecting groups which can be cleaved off under alkaline or ammoniacal conditions; the fluorenylmethoxycarbonyl group or the trifluoroacetyl group have proven to be particularly favourable.

The compounds of the formula I can be produced from a compound of the formula II

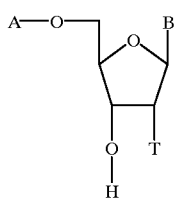 (II)

in which

A represents an oxygen protecting group, a nucleotide or an oligonucleotide,

B represents a natural or modified nucleobase and

T represents hydrogen, lower alkyl, azide, lower alkyloxy or a hydroxy group which is protected if desired, with a phosphane of the formula III

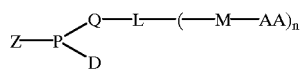 (III)

in which

Z represents a good leaving group;

Q represents oxygen or sulphur;

L represents a (n+1) valent bridging link;

M is selected from the group consisting of oxygen, sulphur, nitrogen or N-H;

n represents a natural number from 1 to 200;

D represents a secondary amine residue; and

AA is a cleavable protecting group.

The reaction conditions can be chosen by one skilled in the art analogous to those already described for the nucleoside phosphoramidites of the state of the art. However, in this process it must be taken care that no reagents are used which when used can cleave off the protecting group AA. These reaction conditions are known to one skilled in the art for the individual protecting groups.

The phosphane of the formula III can be synthesized in a simple way from commercially available starting materials. In the preferred order of the production reactions the reaction with a secondary amine is scheduled first since this is a cheaper raw material. Thus in this reaction step losses in yield by unspecific reaction can if necessary be accepted. The phosphane of the formula III is preferably produced in that a compound of the formula (VI)

$P(-Z)_3$ (VI)

in which Z represents a good leaving group is reacted with a secondary amine of the formula (VII)

H-D (VII)

in which

D represents a secondary amine residue and the product is allowed to react with the compound of the formula VIII H-Q-L($-$M-AA)$_n$ (VIII)

in which

Q represents oxygen or sulphur,

L represents a (n+1) valent bridging link,

M represents oxygen, sulphur, nitrogen or N-H,

AA represents a protecting group which can be cleaved off, n represents a natural number from 1 to 200 and the product formed is isolated. The residue Z is preferably halogen and particularly preferably chlorine.

Compounds of the formula VII are in particular secondary amines known to one skilled in the art of the formula $H-NR^1R^2$ in which $R^1$ and $R^2$ are the same or different and primary, secondary or tertiary alkyl residues with 1–10 carbon atoms or together, if desired, represent an alkyl-branched cycloalkyl residue with 5–7 carbon atoms which can contain one or two nitrogen, oxygen and/or sulphur atoms as heteroatoms or N $R^1$ $R^2$ represents an imidazolyl, triazolyl, tetrazolyl, 3-nitro-1,2,4-triazolyl, thiazolyl, pyrrolyl, benztriazolyl or benzhydroxytriazolyl residue. Diisopropylamine and morpholine have proven to be particularly preferable amines.

The term phosphane, as used in this invention, means a compound containing a trivalent phosphorus.

Linear or branched, saturated or unsaturated hydrocarbons with 1–10, preferably 2 to 6 carbon atoms are worthy of mention as the bridging link. The hydrocarbon chain can be interrupted by heteroatoms, for example oxygen or sulphur. The bridging link can also contain aliphatic or aromatic ring systems. The bridging link can also have further heteroatoms. However, with regard to the reactions which are to be carried out in the process according to the present invention with compounds which contain this bridging link, those bridging links must, however, be excluded which have free unsubstituted or primary amino groups or hydroxy groups as substituents. The bridging link is connected through n covalent bonds with n groups M. The preferred number of n is from 1 to 200, most preferred from 1 to 5.

The compounds of the formula III have the advantage compared to the phosphanes of the state of the art that they can be used for the synthesis of nucleoside phosphoramidites for the phosphoramidite synthesis of nucleic acids as well as having a reactive group in a protected form; this can serve as a linkage site for detectable residues.

The process according to the present invention for the production of nucleotide sequences includes in particular the following steps:

Coupling reaction of a nucleoside phosphoramidite of the formula I with a nucleoside which has a free hydroxy group. The nucleoside with the free hydroxy group is preferably bound covalently to a solid carrier. The other reactive groups of the nucleoside such as amino groups, carbonyl groups or further hydroxy groups are preferably protected by protecting groups which are stable under the conditions of the coupling reaction. Preferably a 2'-hydroxy group which may be present on the sugar residue is protected by a t-butyldimethylsilyl group. The free hydroxy group is preferably the 5'-hydroxy group of the sugar residue.

The nucleoside can be a mononucleoside, an oligo- or polynucleotide. It is, however, preferably a mononucleoside, oligo- or polynucleotide of 2 to 200, preferably 20 to 60 nucleotide building blocks. The nucleotide building blocks can be natural or modified nucleotides.

The nucleoside can also be a nucleoside modified in a manner according to the present invention.

Afterwards the nucleotide sequence bound to the solid phase is oxidized. Iodine has proven to be a preferred oxidizing agent.

Subsequently a capping step is preferably carried out. This is carried out according to known methods.

Selective cleavage of the protecting group A or the oxygen protecting group of the terminal 5'-hydroxy group of the nucleotide or oligonucleotide of the residue E. In the preferred case, if the oxygen protecting group of the residue E is a protecting group such as a dimethoxytriphenylmethyl group which can be cleaved off under acid conditions it can be cleaved off for example by dichloroacetic acid.

These first steps can now be repeated, if desired. For this a conventional mononucleoside phosphoramidite or one having formula I can be used as the mononucleoside phosphoramidite.

As soon as the desired length of the nucleotide sequence has been reached, the protecting groups AA are cleaved off. In the case of the amino protecting group the trifluoroacetyl or the fluorenylmethoxycarbonyl residue (Fmoc) has proven to be particularly advantageous.

Subsequently the nucleotide sequence is cleaved off from the solid carrier in a known way. The conditions are chosen according to the type of covalent bond and are not influenced by the modification according to the present invention.

Those conditions are, however, particularly preferred under which the cleavage of the protecting group AA and the cleavage of the nucleotide sequence from the carrier occur simultaneously. This can, for example, be effected by use of a carrier bound via a 3'-O-succinyl to CPG (controlled pore glass) and the Fmoc protecting group as residue AA in which alkali, preferably concentrated aqueous ammonia solution or amine solution, is used as the cleavage reagent.

Usually a purification step follows, for example a purification by means of HPLC chromatography or/and a dialysis. The same conditions apply here as those usually used for oligonucleotide synthesis.

All these steps have in common that, apart from the fact that another nucleoside phosphoramidite is used and that instead of the reagents to cleave off the oxygen protecting groups at the phosphate residue the prior art reagents for the cleavage of the protecting group AA are used, no changes in the conventional course of the process need to be carried out. In particular the number of steps is the same as, or smaller than, in the conventional phosphoramidite process. Thus the process according to the present invention can be carried out in the available nucleic acid synthesizers for the phosphoramidite synthesis without changes in apparatus.

The nucleotide sequence of formula IX prepared in this way preferably has 2 to 200, particularly preferably 20 to 60 nucleotide building blocks. Of these 10 to 80%, particularly preferably 20 to 50%, of the nucleotide building blocks are nucleotide building blocks formed from the nucleoside monophosphates of formula I modified at the phosphorus atom as indicated by brackets [] in formulae V and IX. These modified nucleotide building blocks are preferably at an interval of 2–5 nucleotides to one another in the sequence. The compounds of formula IX have many uses.

For example nucleotide sequences can be prepared in a simple manner from the nucleotide sequences of formula IX prepared according to the present invention which have a detectable residue or a residue which can be converted into a detectable residue. If the nucleotide sequence has several modified nucleotide building blocks, nucleotide sequences can be prepared which contain several such residues. This case is preferred since it has been proven that as a result the determination of nucleic acids becomes more sensitive.

A further object of the invention is therefore a process for the preparation of a nucleotide derivative of formula V

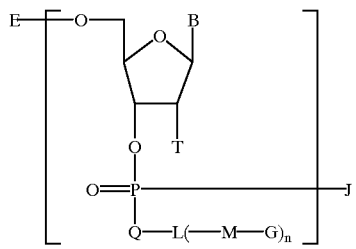

(V)

wherein

E is selected from the group consisting of hydrogen and a phosphorous atom in the phosphate residue of an adjacent nucleotide or oligonucleotide;

J is selected from the group consisting of hydroxy, a 5' oxygen atom of the sugar of an adjacent nucleotide or oligonucleotide and an oxygen chemically bound to a carrier;

B is a natural or modified nucleobase;

T is selected from the group consisting of hydrogen, hydroxy, lower alkyl, lower alkyloxy and azide;

Q is oxygen or sulfur;

L is a (n+1) valent bridging link;

M is selected from the group consisting of oxygen, sulfur, nitrogen and NH;

G is a detectable residue or a residue convertible to a detectable residue;

n is a natural number from 1 to 200;

comprising reacting subsequent to the above mentioned steps a nucleotide sequence of formula IX

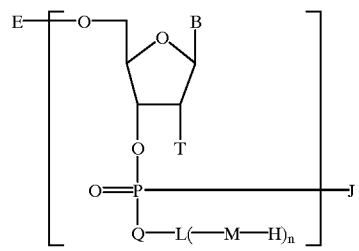

(IX)

wherein E, J, B, T, Q, L, M and n are as defined above with a compound of formula IV

ZZ-G        (IV)

wherein

ZZ is a reactive group, and

G is as defined above.

A nucleophilic group which can be easily substituted or an electrophilic group are for example possible as the reactive group ZZ Compounds of formula IV are for example carboxylic acid halides.

Electrophilic groups are for example the groups in activated esters or anhydrides. A preferred ester is for example the N-hydroxysuccinimide ester of haptens, if these have a carboxyl group.

The further nucleotide encompassed in the meaning of the residues E or J can be a natural or a modified nucleotide. The nucleotide sequence encompassed in the meaning of residues E or J can contain natural as well as modified nucleotide building blocks. The nucleotide sequence of formula V has preferably 2 to 200, particularly preferably 20 to 60 nucleotide building blocks. Of these 10 to 80%, particularly preferably 20 to 50%, of the nucleotide building blocks are nucleotide building blocks formed from the nucleoside monophosphates of formula I.

The residue G can be a low as well as a high molecular weight structure. Preferred low molecular reporter weight molecules are dyes and haptens; preferred high molecular weight groups are e.g. enzymes or immunologically active substances such as antigens or antibodies. Haptens are particularly preferred. Of these, those are particularly preferred which do not occur under normal conditions in body fluids such as digoxigenin for example. Haptens and in particular digoxigenin have proven to be particularly advantageous as the immunologically active substance since the molecular weight of nucleotide sequences which have these is not changed much by the modification and can thus be used as a standard of length, for example, in gel chromatography.

It has turned out that the process according to the present invention for the production of nucleotide sequences has in addition the following advantages compared to the state of the art:

Because the modification is introduced at the phosphorus atom the base-pairing of the nucleotide sequence formed with a complementary nucleotide sequence is not impaired.

The nucleotide sequences formed are accepted as primers by polymerases.

The modification can be introduced in addition to other modifications, for example, of the sugar residue or of the base, or in addition to 3'- or 5'-end labels.

The process includes a convergent synthesis of the necessary building blocks. Such processes are particularly advantageous because the yields, in particular of the expensive nucleotide building blocks, can be kept high.

The readily-available, naturally-occurring β nucleosides can be used for the synthesis of the nucleoside phosphoramidites.

It was possible with the same or even a reduced number of reaction steps to utilize the well-known advantages of the solid-phase phosphoramidite process for the synthesis of nucleotide sequences in order to synthesize nucleotide sequences modified at the phosphate residue.

Using the process according to the present invention it is possible to introduce a very special number of modifications at quite specific sites in the sequence.

The modified nucleotide sequence formed can be used universally. For example different detectable residues can be chosen.

Because the detectable residues are not present from the beginning in the nucleoside phosphoramidites, complications are avoided during the chemical synthesis of the nucleotides which would be expected when using enzyme labels or other sensitive reporter groups.

The steric hindrance by reporter molecules can reduce the yield and efficiency of oligonucleotide syntheses. This disadvantage is avoided in the process according to the present invention.

The nucleotide sequences of formula V can be used advantageously as the nucleotide sequence complementary to the sample DNA in methods for the detection of nucleic acids in a sample by bringing the sample into contact with a nucleic acid which is essentially complementary to it, treatment of the mixture under conditions which lead to the hybridization of nucleic acids which are complementary to one another and detection of the detectable residue. The detection of the detectable residue can be effected by known methods. If the detectable residue is an immunologically active substance then the residue can be reacted with a labelled immunological partner. Afterwards the label is measured. In the case of this use of the nucleic acid according to the present invention haptens, in particular digoxigenin, are preferred as the residue W.

They are equally suitable as primers in the enzymatic synthesis of double-stranded nucleic acids from single-stranded nucleic acids. The double-stranded nucleic acid which forms then contains the nucleotide sequence in at least one of the two strands.

The invention is elucidated by the following non-limiting Examples.

EXAMPLE 1

2-(9-fluorenylmethoxycarbonyl-)aminoethanol 68.0 g (ca 200 mMol) 9-fluorenylmethoxycarbonyl-N-hydroxysuccinimide ester (Fmoc-O-Su) is dissolved with stirring in 300 ml dioxan in a 1 l round-bottomed flask. 40 g $Na_2CO_3$ dissolved in 200 ml water as well as 14.4 ml (238 mMol) ethanolamine are added successively to the clear solution. The pulpy reaction mixture which forms at once is stirred overnight at room temperature and is aspirated on the following day. The filtration residue which contains unreacted Fmoc-O-Su, N-hydroxy-succinimide as well as the desired product, is recrystallized from ethyl acetate. After drying in a vacuum 47.4 g pure product=76% of the theoretical yield are obtained.

$^1$H-NMR (ppm) (DMSO):3.4 (m, $CH_2O$, 2 H); 3.6 (t, $CH_2N$, 2H); 4.2–4.5 (m, $CH_2OCO+H$ [C9], 3 H); 5.2 (s [b], NH, 1 H); 7.2–7.9 (m, aromatic, 8 H);

EXAMPLE 2

Dichloro-N,N-diisopropylamino-phosphane 300 ml abs. ether, 81 ml anhydrous pyridine and 87.5 ml $PCl_3$ (1 Mol) are pre-cooled with stirring to −70° C. in a 2 l three-neck, round-bottomed flask with a 500 ml dropping funnel, KPG stirrer, thermometer and acetone/dry ice bath. 142 ml diisopropylamine (1 Mol) in 250 ml abs. ether are added dropwise to it within 2 hours and the temperature is maintained at ca −60 to −65° C. After completing the addition, the thickened pulpy reaction mixture is allowed to reach room temperature and is diluted with about 600 ml abs. ether to make it more easily stirrable. After a further 3 hours stirring at room temperature the precipitate which forms is aspirated over a glass filter and washed several times with ether. After drawing off the ether at normal pressure, it is freed of unreacted $PCl_3$, diisopropylamine and pyridine in a water-jet vacuum and then the remaining oil is fractionally distilled under an oil-pump vacuum ($K_p$ 46° C./0.35 Torr). 73.4 g of the phosphane is obtained which corresponds to 36% of the theoretical yield.

31P-NMR (ppm) ($CHCl_3$):167.5

EXAMPLE 3

2-(9-fluorenylmethoxycarbonyl-)aminoethyl-N,N-diisopropylamino-phosphochloridite 0.9 ml dichloro-N,N-diisopropylamino-phosphane (5 mmol) is dissolved in 30 ml abs. tetrahydrofuran in a 100 ml round-bottomed flask and 0.4 ml anhydrous pyridine is added to this. A solution of 1.4 g 2-(9-fluorenylmethoxycarbonyl)aminoethanol (5 mmol) in 20 ml abs. tetrahydrofuran is added slowly dropwise to this mixture during ca. 5 hours while stirring magnetically. After aspirating the pyridine hydrochloride which separates out and drawing off under vacuum the tetrahydrofuran, the remaining oil, (2.2 g=98% of the theoretical yield) is used directly for the preparation of the nucleoside phosphoramidite (see Example 4).

EXAMPLE 4

5'-O-dimethoxytrityl-2'-deoxythymidine-3'-O-[2-(9-fluorenylmethoxycarbonyl)aminoethyl]-N,N-diisopropylamino-phosphane a) 2.5 g 5'-O-dimethoxytrityl-2'-deoxythymidine (4.6 mMol) is dissolved in 50 ml dichloromethane (distilled over $Na_2CO_3$) as well as 2.5 ml N-ethyl-N,N-diisopropylamine in a 100 ml round-bottomed flask. 2 ml 2-(9-fluorenylmethoxycarbonyl-) aminoethyl-N,N-diisopropylamino-phosphochloridite (ca. 5 mmol) is added to this using a disposable syringe. It is stirred for 48 hours at room temperature and evaporated down in a vacuum to a viscous residue.

The crude product is purified by chromatography on silica gel 60 (column 30×2 cm, mobile solvent petroleum ether 50–75° C./ethyl acetate/dichloromethane/pyridine=4:8:8:2). The fractions containing product are collected and the solvent is completely removed in a vacuum.

0.9 g of a white foamy residue is obtained corresponding to 20% of the theoretical yield.

b) In an alternative process 5.45 g 5'-O-dimethoxytrityl-2'-deoxythymidine (10 mmol) is dissolved with stirring in 100 ml absolute dioxane. A solution of 2.7 g bis-(diisopropylamino)-chlorophosphane (10 mmol) which was prepared according to S. Hammoto, H. Takaku, Chemistry Lett. 1986, 1401–1404 and 2.1 ml triethylamine (15 mmol) in 100 ml dioxane are added dropwise to this within 30 minutes. The reaction is followed by thin layer chromatography in methylene chloride/ethyl acetate=1:1 as the mobile solvent. After 2 hours the precipitate of triethylammonium-chloride is filtered off under the protective gas argon and the filtrate is concentrated (colourless foam). The 5'-O-dimethoxytrityl-2'-deoxythymidine-3'-O-bis-(N,N-diisopropylamino)phosphane formed is converted to the desired product without further isolation. For this the colourless foam is taken up in 100 ml absolute acetonitrile and 3 g 2-(9-fluorenylmethoxycarbonyl)-amino-ethanol (Example 1) as well as 35 mg (5 mmol) tetrazole (sublimed) are added. It is stirred overnight at room temperature and the reaction is terminated by addition of 100 ml ethyl acetate. After extracting three times with saturated sodium chloride solution the combined organic phases are dried over sodium sulphate. After filtering off the sodium sulphate the filtrate is concentrated. The crude product is purified by chromatography on silica gel 60 H: (1=24 cm, d=4 cm; mobile solvent: methylene chloride/ethyl acetate=5:1). After removal of the solvent a colourless foam is again obtained. This is taken up in 10 ml methylene chloride and precipitated with 400 ml ice-cold n-hexane. 1.8 g of the desired product is obtained as a colourless powder which corresponds to 20% of the theoretical yield.

The two diastereomers can be distinguished by TLC as well as by 31P-NMR:
Rf-value ($CH_2Cl_2$/EA=1:1): 0.04, 0.15
31P-NMR (ppm) ($CD_3CN$): 146.7, 145.8

EXAMPLE 5

Synthesis of d ($Tp_{AE}TpTpTpTpTpTpTp_{AE}T$)

The synthesis of the oligonucleotide was carried out on a 1 µmol scale according to a standard protocol in a fully automated DNA synthesizer 8600 from the BioSearch company. The synthesis instrument is equipped for this with a reaction column coated with 1 µmol thymidine carrier and in a first reaction step the 5'-OH protecting group (dimethoxytrityl-) is cleaved off by treatment with a 2% dichloroacetic acid solution in dichloromethane. After washing the column with acetonitrile, the 5'-O-dimethoxytriphenylmethyl-2'-deoxythymidine-3'-O-[2-(9-fluorenylmethoxycarbonyl)aminoethyl]-N,N-diisopropylamino-phosphane of Example 4 modified at the P according to the present invention is coupled to the free 5'-OH group of the starting nucleoside and at the same time is activated with tetrazole in acetonitrile. The P atom which is still present in the trivalent form is converted after renewed washing into the natural pentavalent phosphate by oxidation with a solution of iodine in $THF/lutidine/H_2O$. The subsequent capping step with acetic anhydride/dimethylaminopyridine blocks the non-coupled 5'-OH-nucleoside by acetylation. By this means the formation of false sequences is suppressed. After washing, the synthesis cycle begins again from the start with a renewed cleavage of the 5'-O-dimethoxytrityl protecting group. In this way 6 thymidine building blocks with an unmodified phosphoramidite moiety are introduced into the reaction sequence, before in the last cycle a further coupling with the aminoethylated thymidine-phosphoramidite ($TP_{AE}$) is carried out. After completion of the synthesis the oligonucleotide bound to the carrier is released by treatment with concentrated aqueous ammonia solution and at the same time the Fmoc protecting group of the aminoethylated phosphate is thereby removed. The result is 86 ODU/$A_{260}$. This crude mixture is processed by HPLC under the following conditions.
Column: Mono Q HR 10/10 (Pharmacia)
Eluant A (water), eluant B (0.5 MLiCl)
Gradient: from A to 50% B in 60 minutes.
The eluate is dialyzed overnight against $H_2O$
(Spektrapor, MWCO 1000)
Yield: 55 ODU

EXAMPLE 6

Labelling of the oligonucleotide from Example 5 with digoxigenin

55 ODU/$A_{260}$ of the oligomer from Example 5 is dissolved in 1 ml 0.1 M Na borate buffer pH 8.5 and mixed with a solution of 10 mg digoxigenin-O-succinyl-amidocaproic acid-N-hydroxysuccinimide ester in 1 ml dimethylformamide. The mixture is stirred for 18 hours at room temperature, evaporated to dryness in a vacuum, dissolved in $H_2O$ and the mixture of products is separated by HPLC:
Column: Shandon Hypersil ODS, 25 cm×0.4 cm
Eluant A: 0.1 M triethylammonium acetate solution
Eluant B: 0.1 M triethylammonium acetate solution/isopropanol
Gradient: from A to 50% B in 30 minutes
The product fraction is concentrated by evaporation in a vacuum, taken up in water and dialyzed overnight against distilled water (Sprectrapor, MWCO 1000)
Yield: 11 ODU/$A_{260}$

EXAMPLE 7

Comparison of the detection limit in DNA tests

The hybridization properties of three identical oligonucleotides (38 mers) with a sequence specific for HIV was tested against a cloned HIV-DNA fragment (954 bp PvuII/BglII fragment from the gag region of the HIV-Wfl.13-isolate). The oligonucleotides are labelled with digoxigenin (dig) at the following sites:

1. One each at a 5'-terminal uracil and at a uracil located in the middle (i.e. two dig labels, base label at C-5 of the uracil).

2. One each at a 5'-terminal, 3'-terminal and at a uracil located in the middle (three-fold dig label, base label at C-5 of the uracil).

3. One each at a 5'-terminal phosphate group and at a phosphate group located in the middle (2 dig labels/molecule, labelling according to the present invention).

a) Hybridization preparation for oligonucleotides with dig label

The sample DNA is either spotted directly onto filters in dilution series of 1 μl volume each or after separation in the agarose gel it is transferred by Southern blot using 20×SSC buffer onto the filters. The fixation is carried out by UV irradiation for 3 minutes.

The filters are pre-hybridized under the following conditions: 1 h at 40° C. in 5×SSC, 0.5% blocking reagent. The subsequent hybridization with dig labelled oligonucleotides is carried out under the following conditions: overnight at 4° C. in 5×SSC, 0.5% blocking reagent, 200 ng oligonucleotide per ml hybridization solution.

The filters are washed afterwards for 4×10 min in 2×SSC, 0.1% SDS at 40° C.

The detection is carried out by using a POD-labelled antibody against digoxigenin, following the instructions of the non-radioactive labelling and detection kit (Boehringer Mannheim GmbH, Cat. No. 1o93657).

b) Results:

Detection limit of the spotted/blotted sample DNA using dig labelled oligonucleotides:

with a two-fold base dig labelled oligonucleotide (1): 1o
with a three-fold base dig labelled oligonucleotide (2): 10 ng
with an oligonucleotide labelled twice with dig via phosphate (3): 1–10 ng

We claim:

1. A process for the preparation of a nucleotide derivative of formula V

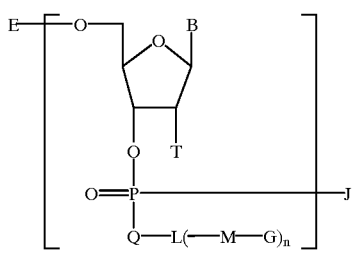

(V)

wherein

E is selected from the group consisting of hydrogen and a phosphorous atom in the phosphate residue of an adjacent nucleotide or oligonucleotide;

J is selected from the group consisting of hydroxy, a 5' oxygen atom of the sugar of an adjacent nucleotide or oligonucleotide and an oxygen chemically bound to a carrier;

B is a natural or modified nucleobase;

T is selected from the group consisting of hydrogen, hydroxy, lower alkyl, lower alkyloxy and azide;

Q is oxygen or sulfur;

L is a (n+1) valent bridging link;

M is selected from the group consisting of oxygen, sulfur, nitrogen and NH;

G is a detectable residue or a residue convertible to a detectable residue;

n is a natural number from 1 to 200;

comprising reacting a nucleotide sequence of formula IX

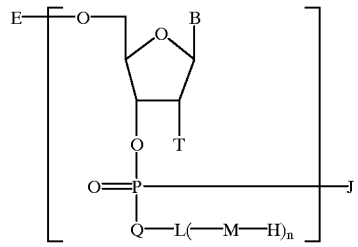

(IX)

wherein E, J, B, T, Q, L, M and n are as defined above with a compound of formula IV

ZZ-G   (IV)

wherein

ZZ is a reactive group, and

G is as defined above.

2. A process according to claim 1, wherein L is a alkyl residue having 1 to 10 carbon atoms.

3. A process according to claim 2 wherein said alkyl residue is a linear alkyl residue.

4. A process according to claim 1, wherein n is 1, 2, or 3.

5. A process according to claim 4, wherein n is 1.

6. A process according to claim 1 wherein G is a hapten residue.

7. A nucleotide sequence of the formula V

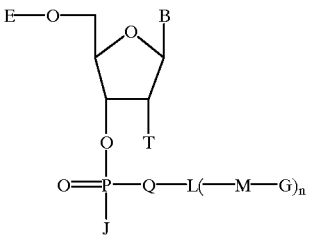

(V)

in which

E is selected from the group consisting of hydrogen and a phosphorous atom in the phosphate residue of an adjacent nucleotide or oligonucleotide;

J is selected from the group consisting of hydroxy, a 5' oxygen atom of the sugar of an adjacent nucleotide or oligonucleotide and an oxygen chemically bound to a carrier;

B is a natural or modified nucleobase;

T is selected from the group consisting of hydrogen, hydroxy, lower alkyl, lower alkyloxy and azide;

Q is oxygen or sulfur;

L is a (n+1) valent bridging link;

M is selected from the group consisting of oxygen, sulfur, nitrogen and NH;

G is a detectable residue or a residue convertible to a detectable residue;

n is a natural number from 1 to 200.

8. A nucleotide phosphoramidite of the formula I

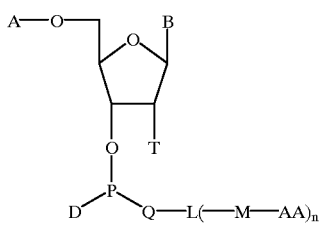
(I)

A is selected from the group consisting of an oxygen protecting group, a nucleotide and an oligonucleotide B is a natural or modified nucleobase;

T is selected from the group consisting of hydrogen, hydroxy, lower alkyl, lower alkyloxy and azide;

Q is oxygen or sulfur;

L is a (n+1) valent bridging link;

M is selected from the group consisting of oxygen, sulfur, nitrogen and NH;

n is a natural number from 1 to 200;

D is a secondary amine residue; and

AA is a cleavable protecting group.

9. Process for the production of a nucleoside phosphoramidite of the formula I by reaction of a compound of the formula II

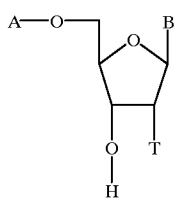
(II)

in which

A represents an oxygen protecting group, a nucleotide or an oligonucleotide,

B represents a natural or modified nucleobase and

T represents hydrogen, lower alkyl, azide, lower alkyloxy or a hydroxy group which is protected if desired, with a phosphane of the formula III

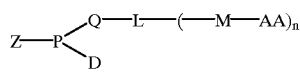
(III)

in which

Z represents a good leaving group;

Q represents oxygen or sulphur;

L represents a (n+1) valent bridging link;

M is selected from the group consisting of oxygen, sulphur, nitrogen or N-H;

n represents a natural number from 1 to 200;

D represents a secondary amine residue; and

AA is a cleavable protecting group.

10. A method for the detection of a nucleotide sequence comprising mixing, under hybridizing conditions, said nucleotide sequence and a complementary nucleotide sequence according to formula (V), wherein

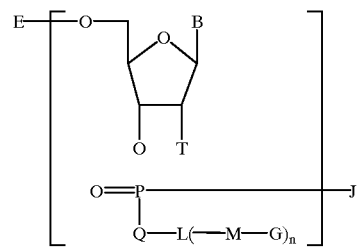
(V)

E is selected from the group consisting of hydrogen and a phosphorous atom in the phosphate residue of an adjacent nucleotide or oligonucleotide;

J is selected from the group consisting of hydroxy, a 5' oxygen atom of the sugar of an adjacent nucleotide or oligonucleotide and an oxygen chemically bound to a carrier;

B is a natural or modified nucleobase;

T is selected from the group consisting of hydrogen, hydroxy, lower alkyl, lower alkyloxy and azide;

Q is oxygen or sulfur;

L is a (n+1) valent bridging line;

M is selected from the group consisting of oxygen, sulfur, nitrogen and NH;

G is a detectable residue or a residue convertible to a detectable residue;

n is a natural number from 1 to 200 and determining the presence of said detectable marker G.

11. A reagent for the detection of a nucleotide sequence comprising a complementary nucleotide sequence according to formula (V)

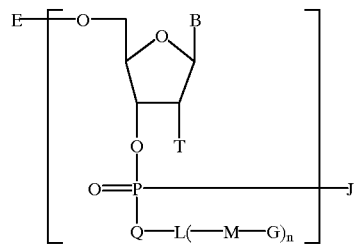
(V)

wherein

E is selected from the group consisting of hydrogen and a phosphorous atom in the phosphate residue of an adjacent nucleotide or oligonucleotide;

J is selected from the group consisting of hydroxy, a 5' oxygen atom of the sugar of an adjacent nucleotide or oligonucleotide and an oxygen chemically bound to a carrier;

B is a natural or modified nucleobase;

T is selected from the group consisting of hydrogen, hydroxy, lower alkyl, lower alkyloxy and azide;

Q is oxygen or sulfur;

L is a (n+1) valent bridging link;

M is selected from the group consisting of oxygen, sulfur, nitrogen and NH;

G is a detectable residue or a residue convertible to a detectable residue;

n is a natural number from 1 to 200.

12. A method for the enzymatic synthesis of a double-stranded nucleic acid comprising the use of a nucleotide sequence according to formula (V)

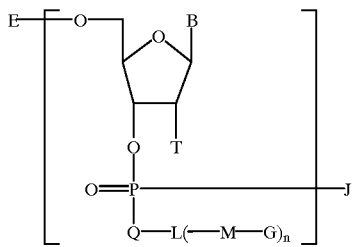

(V)

wherein

E is selected from the group consisting of hydrogen and a phosphorous atom in the phosphate residue of an adjacent nucleotide or oligonucleotide;

J is selected from the group consisting of hydroxy, a 5' oxygen atom of the sugar of an adjacent nucleotide or oligonucleotide and an oxygen chemically bound to a carrier;

B is a natural or modified nucleobase;

T is selected from the group consisting of hydrogen, hydroxy, lower alkyl, lower alkyloxy and azide;

Q is oxygen or sulfur;

L is a (n+1) valent bridging link;

M is selected from the group consisting of oxygen, sulfur, nitrogen and NH;

G is a detectable residue or a residue convertible to a detectable residue;

n is a natural number from 1 to 200 as a primer.

* * * * *